(12) United States Patent
Hirsch et al.

(10) Patent No.: US 6,648,122 B1
(45) Date of Patent: Nov. 18, 2003

(54) APPARATUS FOR TRANSFERRING ARTICLES

(75) Inventors: John L. Hirsch, Sheboygan Falls, WI (US); John A. McCabe, Sheboygan Falls, WI (US)

(73) Assignee: Curt G. Joa, Inc., Sheboygan Falls, WI (US)

(*) Notice: Subject to any disclaimer, the term of this patent is extended or adjusted under 35 U.S.C. 154(b) by 381 days.

(21) Appl. No.: 09/695,961

(22) Filed: Oct. 25, 2000

(51) Int. Cl.7 .............................................. B65G 47/31
(52) U.S. Cl. .................. 198/377.08; 198/404; 198/408; 198/459.2; 198/471.1; 156/552; 156/568
(58) Field of Search ................................ 156/494, 459, 156/519, 552, 475, 481, 567, 568; 198/407, 408, 377.04, 377.08, 459.1, 459.2, 471.1, 689.1, 803.5

(56) References Cited

U.S. PATENT DOCUMENTS

| | | |
|---|---|---|
| 2,702,406 A | 2/1955 | Reed |
| 4,394,898 A | 7/1983 | Campbell |
| 4,726,876 A | 2/1988 | Tomsovic, Jr. |
| 4,880,102 A | 11/1989 | Indrebo |
| 4,925,520 A | 5/1990 | Beaudoin et al. |
| 5,000,806 A | 3/1991 | Merkatoris et al. |
| 5,025,910 A | 6/1991 | Lasure et al. |
| 5,308,345 A * | 5/1994 | Herrin .......................... 156/164 |
| 5,545,285 A * | 8/1996 | Johnson ....................... 156/494 |
| 5,556,504 A | 9/1996 | Rajala et al. |
| 5,560,793 A * | 10/1996 | Ruscher et al. ............. 156/164 |
| 5,788,797 A * | 8/1998 | Herrin et al. ............. 156/308.4 |

* cited by examiner

*Primary Examiner*—Joseph E. Valenza
*Assistant Examiner*—Mark A. Deuble
(74) *Attorney, Agent, or Firm*—Ryan Kromholz & Manion, S.C.

(57) ABSTRACT

An apparatus for transferring articles such as absorbent cores or disposable diaper chassis components from a rotary mechanism, such as a pad turner, to a linear mechanism, such as a conveyor for further processing. The invention provides a device for picking an article from the outside of a toroidal surface, thence extending transversely under tension the article to be transferred so that at the point of deposition the article is held flat and at full length. The device is of particular benefit where an article to be transferred is subject to internally biasing elastic forces.

15 Claims, 8 Drawing Sheets

APPARATUS FOR TRANSFERRING ARTICLES

BACKGROUND OF THE INVENTION

This invention relates to apparatus for transferring articles such as absorbent pads in the manufacture of disposable absorbent articles such as diapers, incontinence control garments or female sanitary pads as they advance along a production line.

In the production and manufacture of disposable products such as sanitary napkins or pants-type diapers, it frequently becomes necessary to manufacture a component of the product in one orientation, and then to rotate that component part 90° so that it is suitably oriented for use in another step in the production process. Various devices have been developed for this purpose and are known to those experienced in the industry. Examples of such apparatus are those described in U.S. Pat. Nos. 4,726,876, 4,880,102 and 5,025,910.

One common method for reorienting such product parts, such as absorbent pads, is to transfer them to a large rotating device, where each part is retained by vacuum on an individual head. The heads each successively pick up one of the parts, are caused to rotate 90° by means of cams or gears, and then caused to deposit the part, after 90° reorientation, onto the next downstream conveyor.

In most applications of this type, the amount of convexity of the vacuum head (i.e., the arc segment angle) is kept to a minimum so as to create the least amount of chord height. This becomes less practical as product length increases, as the required diameter of the turning drum becomes unreasonably large. As the chord height becomes larger, the machine designer must find a compromise between the need for maintaining control of the ends of the product and the need for achieving a firm placement of the product's center section.

Additionally, the product being transferred may possess certain contractile forces which tend to cause unwanted retraction of the ends of the pads during the transfer process.

SUMMARY OF THE INVENTION

It is an object of this invention to solve the aforementioned problems typically associated with transfer devices. In accord with an important aspect of the invention, the product is picked up from a toroidal or convex surface and placed on a flat surface while being, in the process, stretched to a fully extended condition. Additionally, it is an object of this invention to provide these capabilities with apparatus requiring a minimum of moving parts. The apparatus of this invention is of particular benefit where an article to be transferred is subject to internally biasing elastic forces, for example, various types of disposable diapers and, especially, absorbent pads used in the manufacture of such diapers, which pads may contain elastic materials.

The invention includes a coordinated set of three aligned vacuum wheels, which pick the products up from the surface of an upstream product turner or conveyor and place the product onto a destination conveyor later in their rotation. The two outermost wheels (outboard wheels) are truncated cones, with their inboard diameters smaller than their outboard diameters. The center, or inboard wheel is cylindrical in shape. In a preferred embodiment, each wheel is provided with a vacuum pattern arranged to positively attract and hold the individual products.

The outboard wheels are canted with respect to the central wheel so that their faces are approximately parallel to the product surfaces at the point of acquisition or picking up of the product. This angle of cant also places the faces of the outboard wheels, when viewed at the deposition point, in a aligned straight line, parallel to and generally in the same tangental plane as the center wheel. At this point, approximately 180° from the acquisition point, the product is deposited onto a traveling destination conveyor where it may be secured by mechanical means, vacuum or adhesive.

As the outboard canted wheels or drums rotate, their vacuum faces move away from the product centerline. This effect serves to stretch the product and pull it to its fully extended length. Inasmuch as the amount of extension of the wheels may exceed the actual maximum length of the product, the intention is that the ends of the product are able to slip across the face of the canted wheels in the event that the extension tensile force exceeds the force required to overcome the effects of friction. As a means of preventing the body of the transferred product from being pulled off of the centerline, the surface materials selected for the center wheel or drum preferably have a higher coefficient of friction with the product than do the surfaces of the canted outboard drums. Alternatively, a higher vacuum level or a more advantageous pattern of vacuum holes may serve to hold the product more securely to the center wheel.

DETAILED DESCRIPTION OF THE INVENTION

Figure 1:
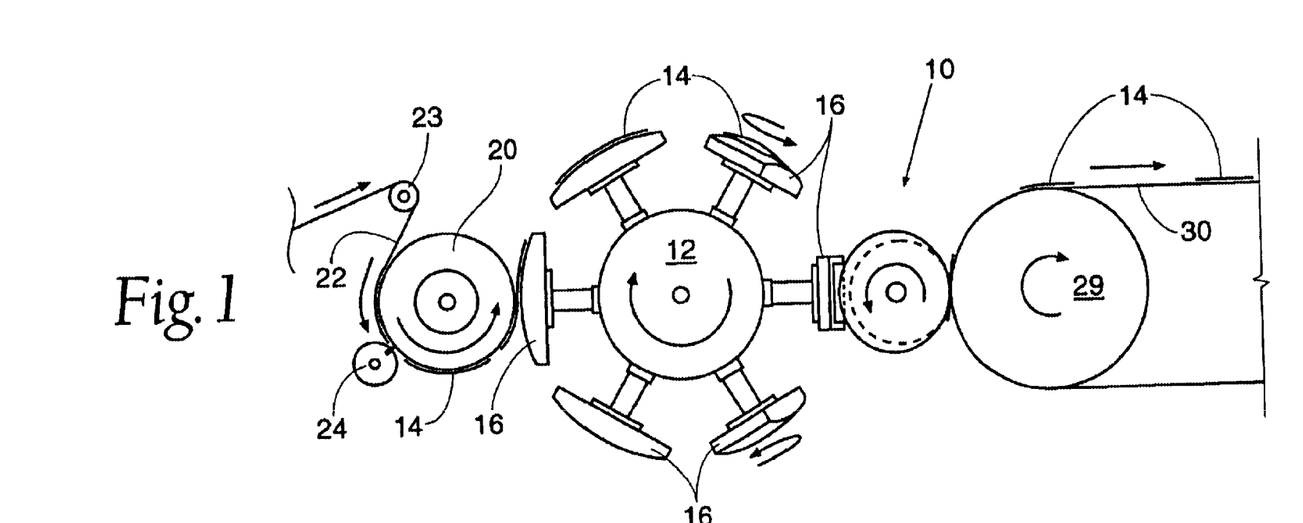
FIG. 1 is a fragmentary side elevational view, shown in somewhat diagrammatic form, of a pad transferring assembly of this invention.

Referring more particularly to the drawings, there is seen in FIG. 1 a transfer device 10 of this invention. Transfer device 10 is adapted to receive a series of articles 14 from a pad turning device 12, which includes a plurality of radially extending transfer heads 16. Device 12, for example, may be a rotary pad turner of the type more fully described in U.S. Pat. No. 5,025,910. Articles 14, such as absorbent pads, may be any elongated articles which need to be rotated 90 degrees during the course of a manufacturing operation. Such pad turning devices are especially needed and are suited for use in connection with the manufacture and packaging of sanitary napkins as well as absorbent pads which are used in the assembly of disposable garments such as adult incontinence garments or children's' training pants.

Also, as seen in FIG. 1, pads 14 are successively and individually picked-up by the transfer heads 16 of pad transfer device 12. In the illustrated embodiment, the pads are picked up from a vacuum drum 20 of which is provided for use, in the nature of an anvil, for cutting a web 22 of absorbent material into individual pads 14 utilizing a rotary cutting device 24 of a type well known in the art. Various conventional conveying and direction changing devices such as rollers 23 may be employed in the feeding of web 22 and do not form a part of this invention.

After the pads 14 have been rotated 90 degrees, they are picked-up by the transfer device 10 of this invention which stretches the articles 14 to their maximum length and deposits them in that condition onto another conveyor 30 as it travels around the outer surface of a drum 29. Conveyor 30 transports the pads for further processing or to a packaging device, as required by a particular application.

Figure 3:
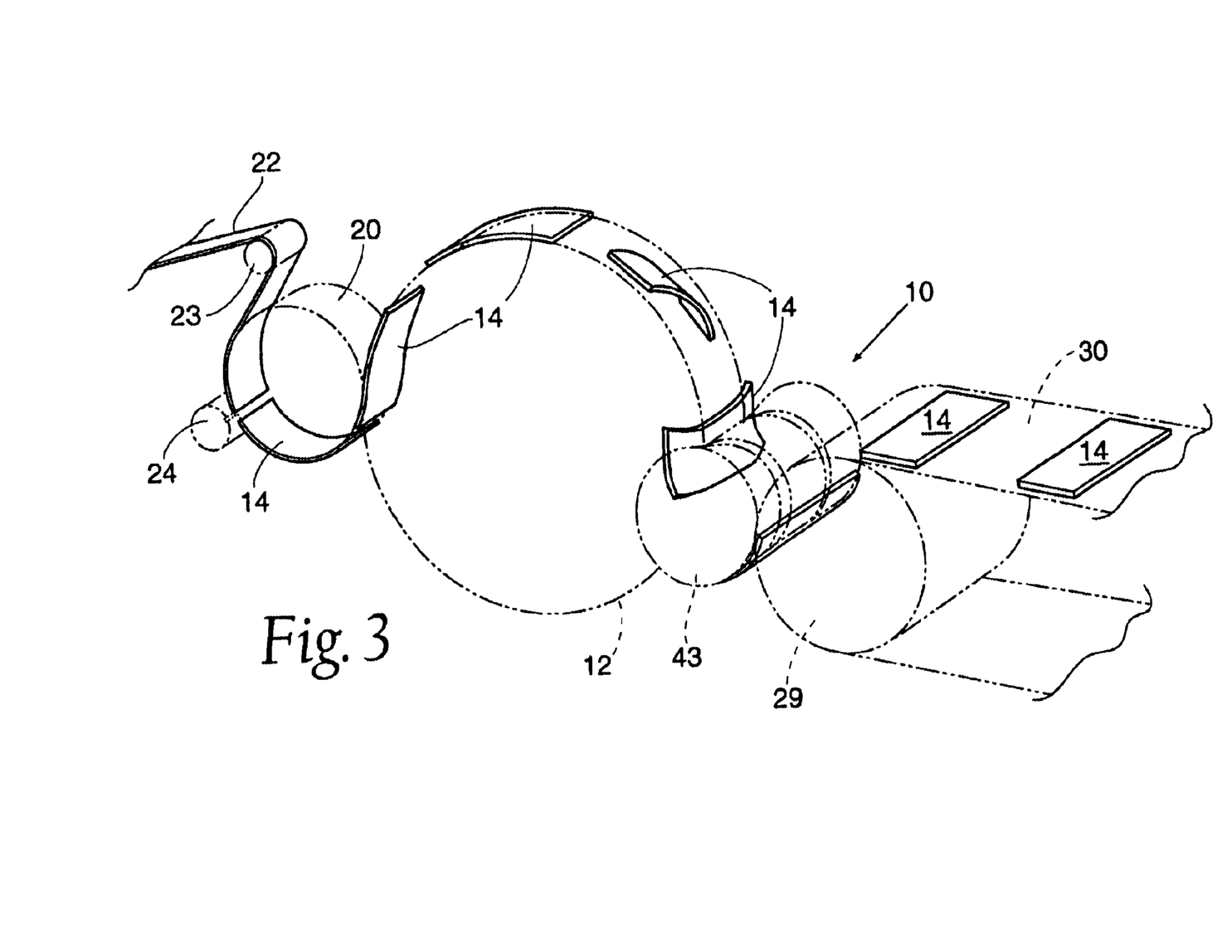
FIG. 3 is a perspective fragmentary, diagrammatic view, showing the related apparatus by means of phantom lines and illustrating the path of movement of pads moving in accordance with the invention.

Referring to FIG. 3, there is seen a diagrammatic depiction of the travel path of the web 22 and the resultant pads 14 which are formed therefrom. In this depiction the apparatus has been eliminated but is partially illustrated by means of phantom lines.

Figure 4:
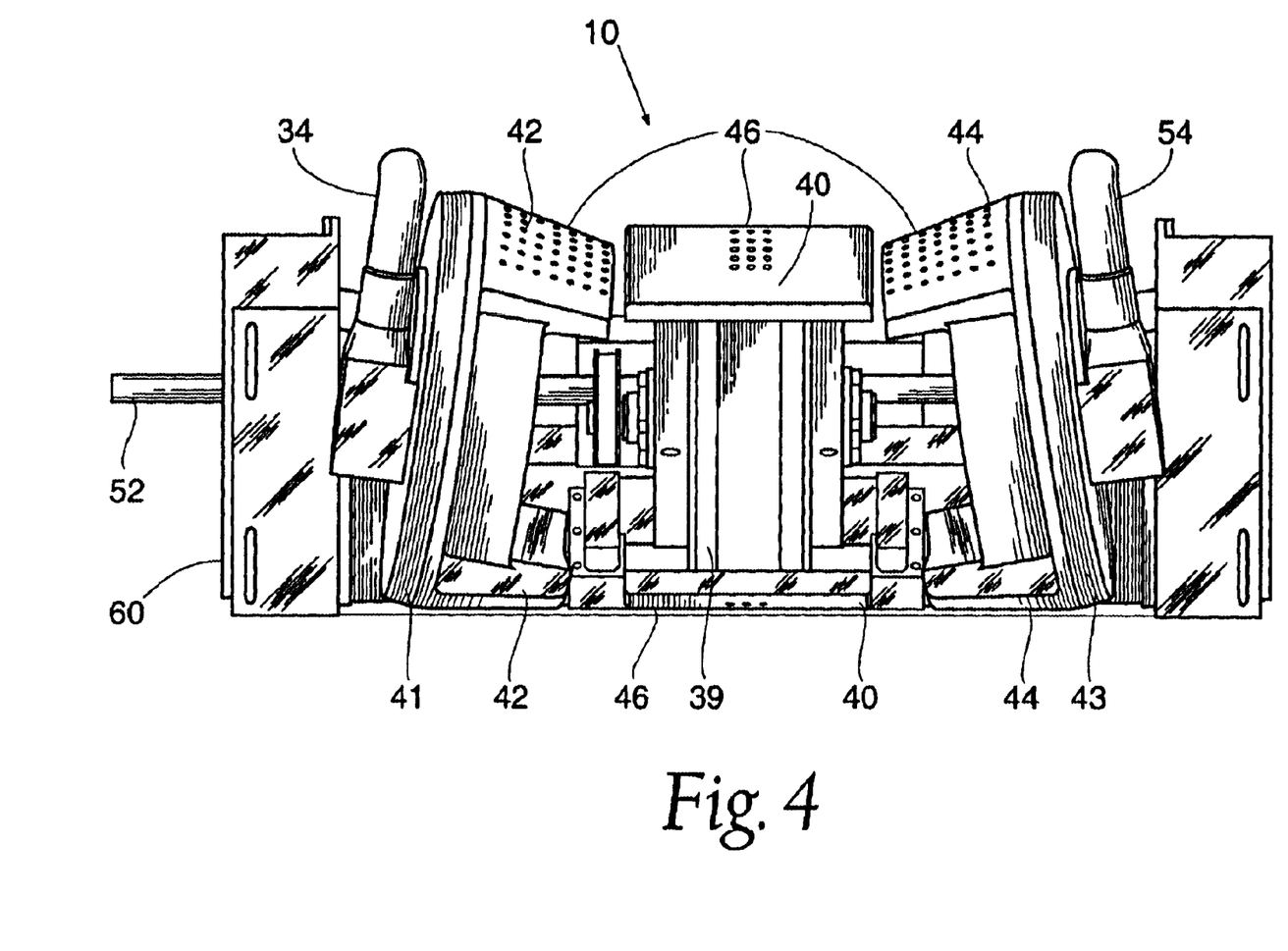
FIG. 4 is a bottom view showing a commercial embodiment of the invention with the pad transfer wheels in the canted position at which pads are picked-up.
Figure 5:
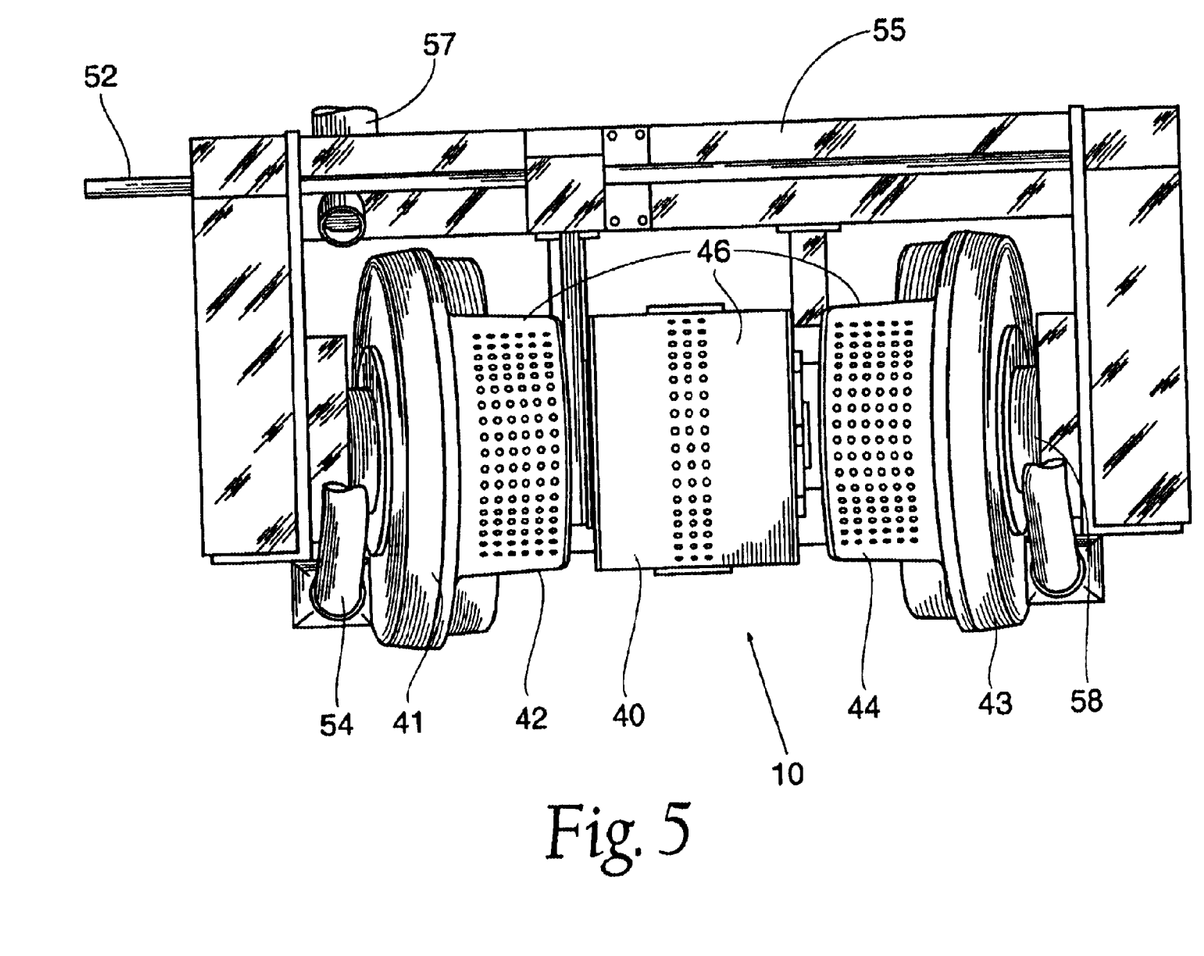
FIG. 5 is a side elevational view of the apparatus of FIG. 4 viewed from an upstream position.

The pad transfer device 10 of this invention is more fully shown in FIGS. 4–8. In FIG. 4 the transfer device 10 is shown, from beneath, in the orientation at which it receives a pad 14 from pad transfer head 16, the pad pickup position also being depicted in FIGS. 2, 7 and 9. Pad transfer device 10 includes a central vacuum drum section 39 which is rotatable about a central axis. A drive shaft 52 rotated by any available power supply system is provided for operation of the apparatus. As illustrated, the central drum section 39 is in the form of a partial segment 40 of a full cylinder wherein those portions of the full cylindrical drum surface which are not necessary for the pad transfer function are omitted.

Also best seen in FIG. 4, are a pair of canted outboard vacuum drum sections 41 and 43. The sections 41 and 43 are in the form of truncated cones, which have their central rotational axis disposed at an oblique angle relative to the central drum section 39. Due to this oblique angle, the faces 42 and 44, of the outboard drum sections 41 and 43, respectively, slope toward the central drum section 39, at the pad acquisition point. Each of the drum section faces 40, 42, and 44 are connected, internally, to a source of vacuum and are provided on their surfaces with openings 46 which, due to the internal vacuum utilized, tend to draw pads 14 toward the partial cylindrical surfaces 40, 42 and 44.

Figure 2:
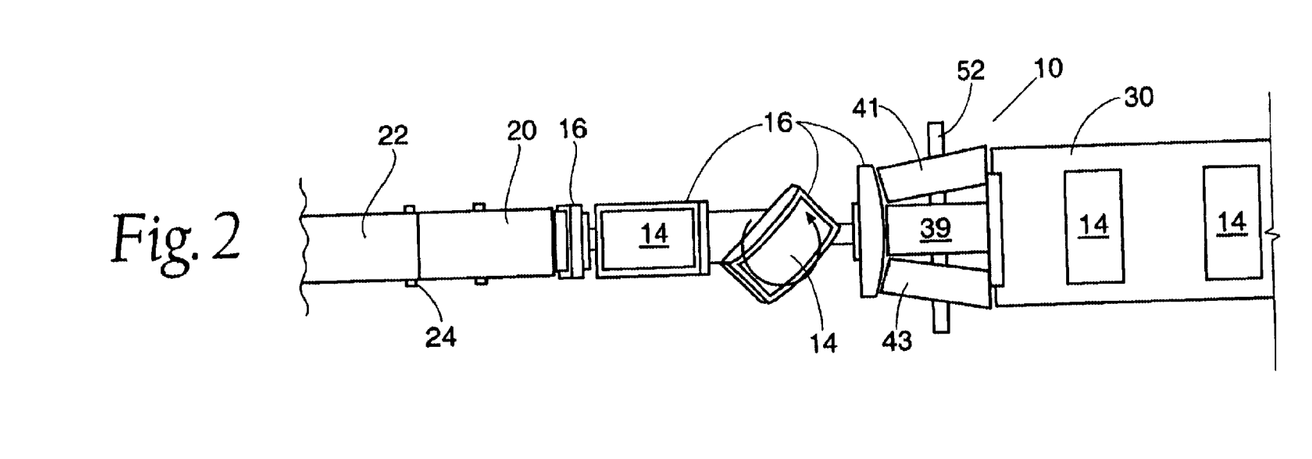
FIG. 2 is a top plan view of the apparatus shown in FIG. 1.

As also seen in FIG. 4 and FIG. 2, the peripheral surfaces 40, 42, and 44 of the drum sections 39, 41 and 43 come into approximate linear alignment with each other at the opposite side of the device, ie., the pad-drop off position, as illustrated. Thus, it will be appreciated that as the transfer device 10 rotates from the position adjacent the transfer heads 16, wherein the drum sections 42, 40, and 44, are in their most concave configuration, to their linear orientation at the drop-off point, the pads 14 which are being transported are, successively, pulled to their maximum linear length.

As also already indicated, the central drum section 40 is provided with a surface having a greater co-efficient friction relative to the pads 14 than the surfaces 42 and 44 of the outer sections. Thus the ends of the products 14 are able to slip across the faces 42 and 44 of the canted wheels when the pad-extending tensile forces exceed the force required to overcome the effects of friction. Thus, as a means of preventing the body of the transferred product 14 from being pulled off of the centerline of the device 10, the surface materials selected for the center wheel or drum preferably have a higher coefficient of friction relative to the product than that of the surfaces of the canted outboard drums. In an exemplary embodiment, the surface of the center section 40 may be formed of a low durometer silicone rubber, while the end sections 42 and 44 may be formed of stainless steel.

Figure 7:
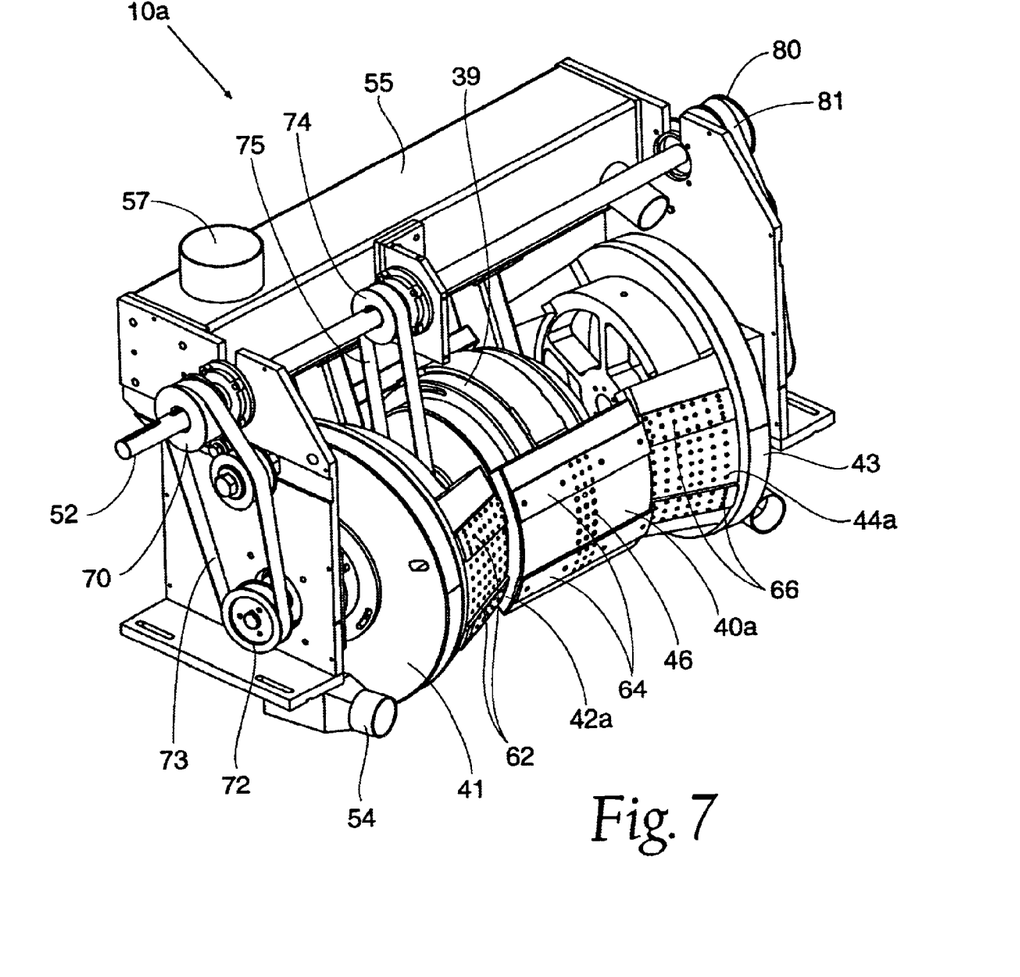
FIG. 7 is a perspective view of the turning drum assembly in accordance with a somewhat modified embodiment of the invention.
Figure 8:
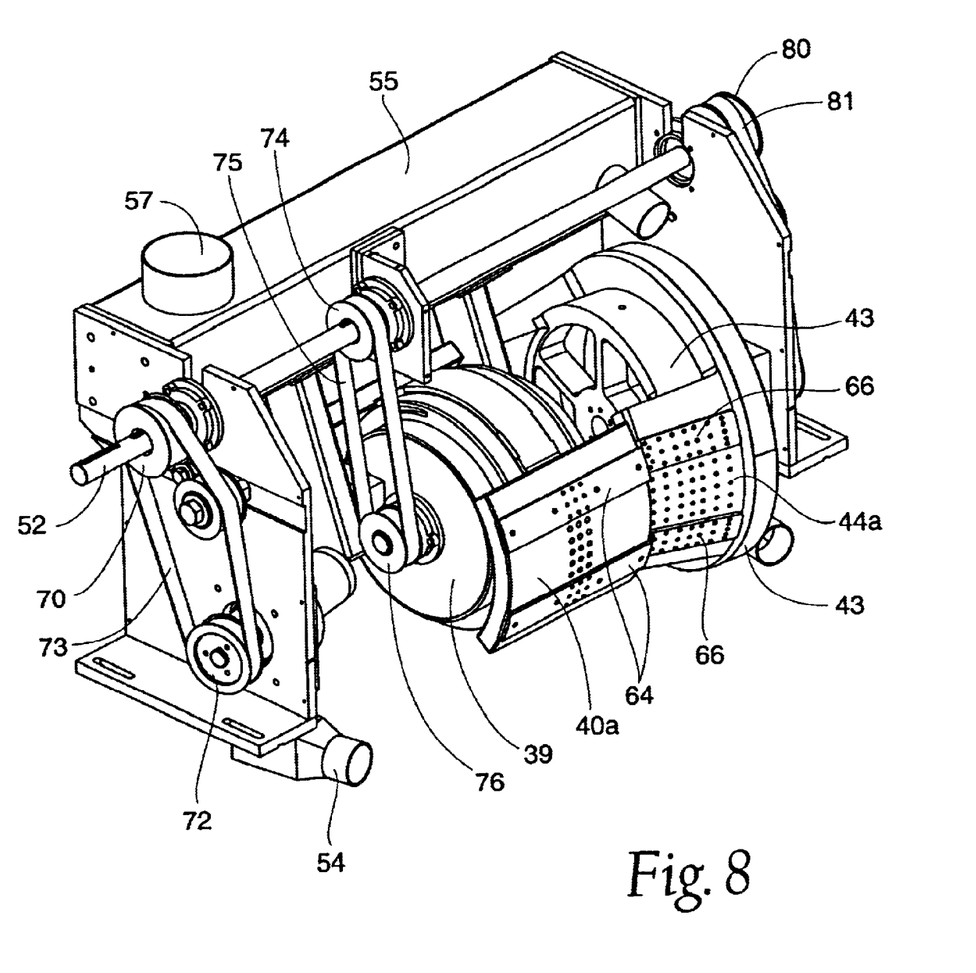
FIG. 8 is a perspective view of the turning drum assembly shown in FIG. 7 with parts removed to reveal the drive system of the assembly and, FIG. 9 is a perspective view of another modified embodiment of the apparatus of this invention.
Figure 9:
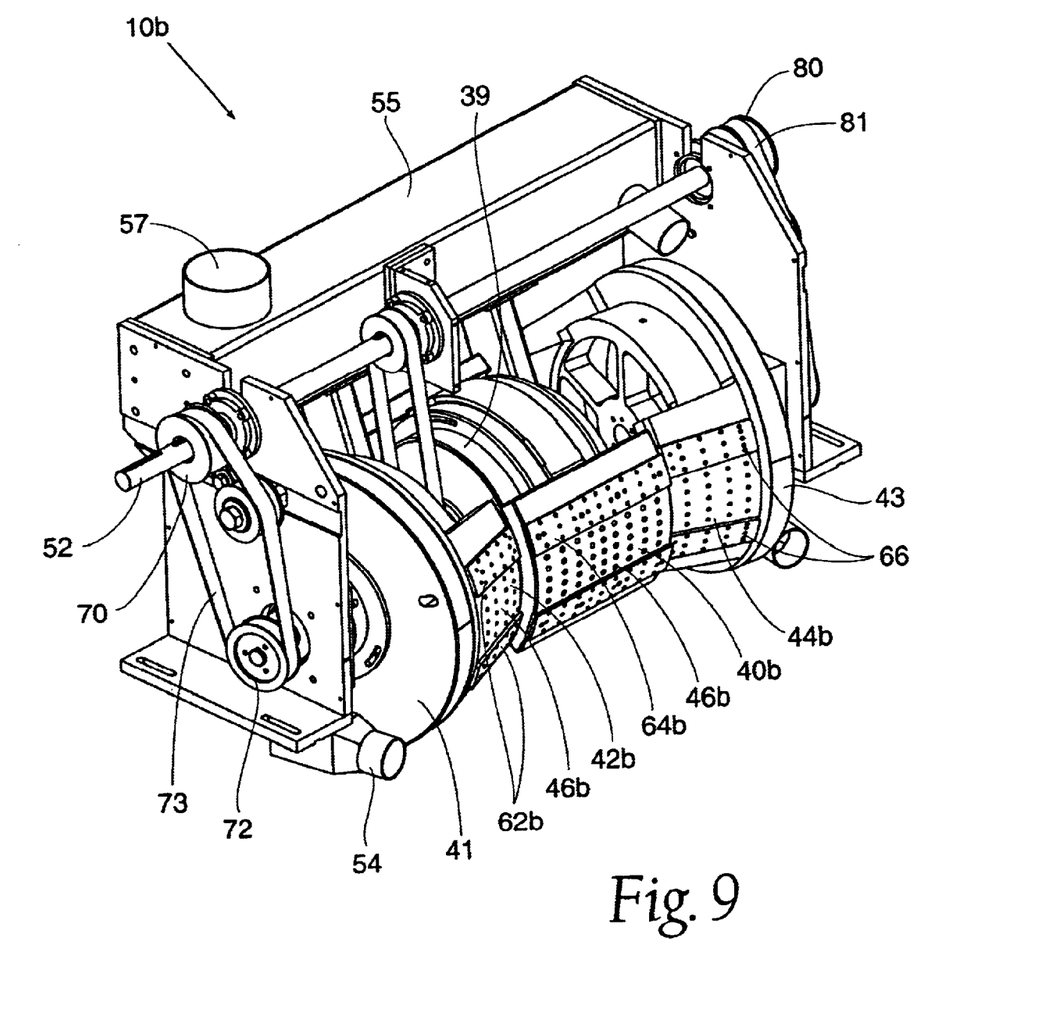

In the modified embodiment of FIGS. 7 and 8 curved plates 62 are attached to the drum surface 42a in an axially extending direction. Similar plates 64 are attached to the outer surface of section 40a and plates 66 are secured to the outer surface of section 44a. Parts which are similar to those of the earlier described embodiment are given the same identifying numerals and are not referred to in detail again in connection with the modified embodiments.

The addition of these axially extending thickened plates 62, 64 and 66 assists in preventing the slippage of transferred articles around the circumference of the drum sections 44a, 42a, and 44a when the sections are rotated. The addition of such thickened sections which preferably have angular corners is of particular assistance if the articles are of a fleecy or low density nature. In the illustrated embodiment these thickened sections are mechanically secured to the drum surfaces, however it will be appreciated that the drum surfaces can be manufactured with the thickened sections, 62, 64 and 66 formed integrally with the drum sections.

Figure 6:
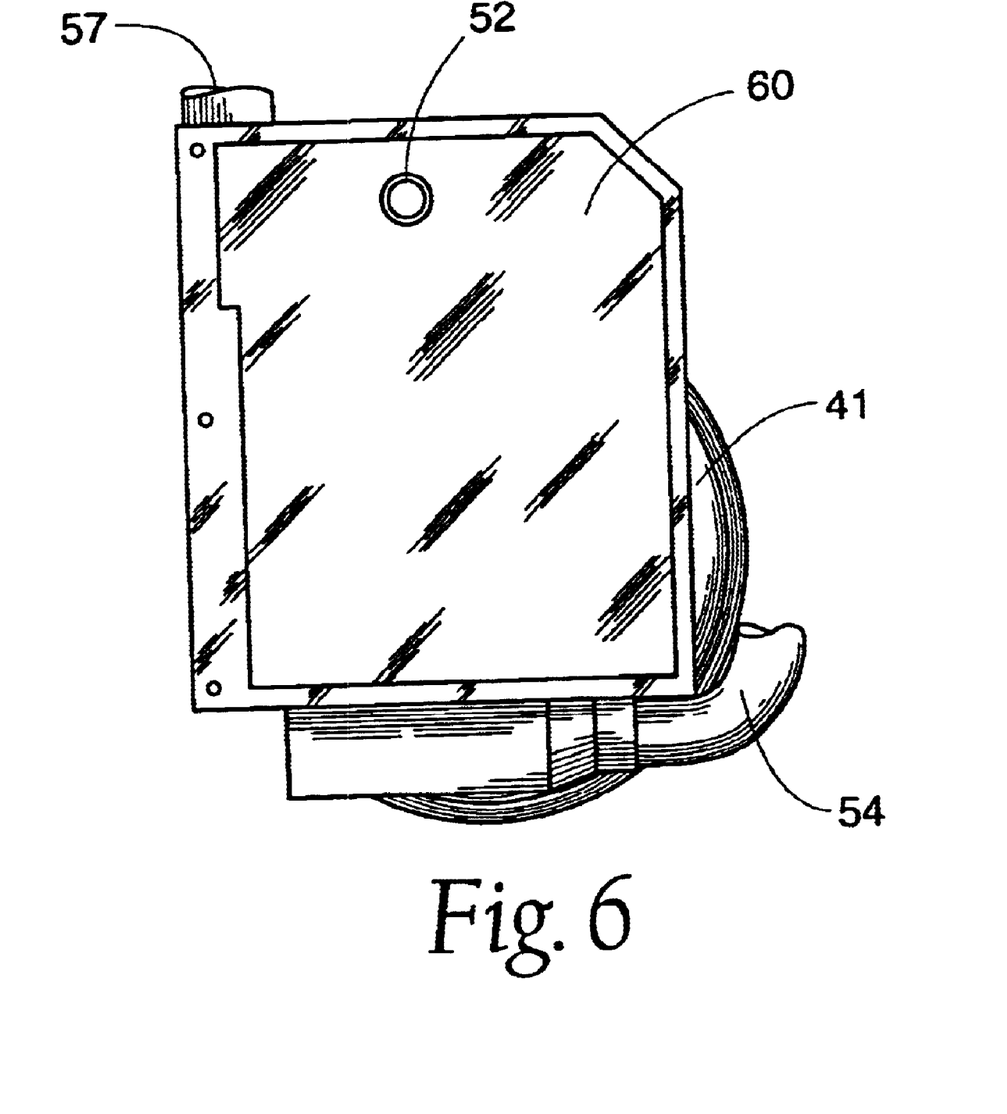
FIG. 6 is an end view of the apparatus of FIG. 4.

Vacuum can be maintained within the interior of the drum sections by means of vacuum drawn through conduits 54 and plenum chamber 55 which is connected via conduit 57 to an available source of vacuum. As seen in FIG. 6, a sheet metal end cover 60 is provided for safety purposes.

Also more fully depicted in FIGS. 7 and 8 are the drive systems for rotation of the drum sections. Section 41, 42a is removed in FIG. 8 to more fully show the drive system. As seen, a rotatable shaft 52 would be driven so as to rotate with the product-making process. A pulley 70 on shaft 52 is used to drive a pulley 72 connected to drum section 41 by means of a conventional drive belt 73. Similarly the middle drum section 39, 40a is driven by the rotatable shaft 52 which is provided with a pulley 74 used to drive pulley 76 by means of drive belt 75. Also in similar fashion, the drum section 43, 44a is driven by a belt 81 which is journaled on pulley 80 and drives a driven pulley (not visible) connected to the drum section 43. The movement of various components of the device described herein are driven in coordination with the related assembly line components depicted in FIGS. 1 and 2, as will be understood by those skilled in the art. In the modified embodiment depicted in FIG. 9, slippage of the articles in an axial direction is minimized by means of a modified array of vacuum openings 46b. As shown, the central drum section 40b and its associated plates 64b are provided with a significantly greater density of openings 46b than are the end sections 42b and 44b and their associated plates 62b and 66b, respecively. In this fashion the force of vacuum applied to the central portion of the assembly 10b is greater than that applied to each end. Hence any tendency of the articles 14 to slip endwise during transfer is minimized.

Although the forgoing illustrative embodiments have been described in detail, the description is intended to be illustrative rather than limiting. Thus the invention may be variously embodied and is to be limited only by the interpretation of the following claims.

We claim:

1. Apparatus for transferring articles from a first moving conveying device and depositing said articles onto a second moving conveyor, comprising:

a central vacuum drum having a longitudinal central axis and being disposed to acquire and transport a central portion of an article to be transferred a pair of canted outboard vacuum drums, each comprising a truncated cone having a central rotational axis disposed at an oblique angle relative to that of said central vacuum drum and adapted to acquire and transport the ends of said article, wherein, due to said oblique angle faces of the outboard drums are sloped toward the center of the article at its acquisition point and are parallel to and generally in a plane with the face of the central drum at the deposition point.

2. Apparatus according to claim 1 wherein said drums are discontinuous and comprise arcuate segments rotatable about a central axis.

3. Apparatus according to claim 1 wherein the surfaces of said outboard drums at the point of deposition are approximately in, but slightly offset from, the plane of the center drum.

4. Apparatus according to claim 1 wherein said outboard drums serve to fully extend the articles as they are rotated.

5. Apparatus according to claim 1 wherein said outboard drums are provided with surfaces having a lesser coefficient of friction with said articles than that of the surface of said central drum.

6. Apparatus according to claim 1 wherein the surfaces of said outboard drums are provided with a lesser concentration of openings for application of vacuum to said articles than is the surface of said central drum whereby endwise slippage of said articles on said apparatus is minimized.

7. Apparatus for picking up an article from the periphery of a generally toroidal surface, stretching said article to a fully extended condition, rotating said article 180° and placing it on a flat moving conveyor surface comprising a central vacuum drum disposed to acquire and transport a central portion of an article to be transferred a pair of canted outboard vacuum drums, each comprising a truncated cone with an inboard diameter smaller than its outboard diameter and having a central rotational axis disposed at an oblique angle relative to that of said central vacuum drum and being adapted to acquire and transport the ends of said article, wherein said oblique angle is such that the faces of the outboard drums are sloped toward the center of the article at its acquisition point and are approximately parallel to and generally in plane with the face of the central drum at the deposition point.

8. Apparatus for successively rotating and transferring articles traveling in an array of discrete articles comprising:

a rotatable drive means including a rotatable hub having a plurality of transfer head assemblies mounted thereon for rotation of the transfer heads around a closed path passing through an acquisition zone where articles are picked up and a discharge zone;

a plurality of radially extending supports disposed around the rotatable hub, each supporting a convexly shaped first transfer device mounted transversely to its respective one of said supports, and rotatable around an axis of said support, a second transfer device located at said discharge zone and being adapted to successively receive articles of said array of discrete articles from said first transfer devices, said second transfer device comprising a central vacuum drum disposed to acquire and transport a central portion of an article to be transferred and a pair of canted outboard vacuum drums, each being in the shape of a truncated cone having a central rotational axis disposed at an oblique angle relative to that of said central vacuum drum and adapted to acquire and transport the ends of said article, wherein said oblique angle is such that the faces of the outboard drums are sloped toward the center of the article at its acquisition point and are approximately parallel to and generally in a plane with the face of the central drum at the deposition point.

9. Apparatus according to claim 8 wherein said drums are discontinuous and comprise arcuate segments rotatable about a central axis.

10. Apparatus according to claim 8 wherein the surfaces of said outboard drums at the point of deposition are approximately in, but slightly offset from, the plane of the surface of the center drum.

11. Apparatus for acquiring a succession of transversely oriented articles from a rotary device, rotating, extending the length of said articles and transferring said articles to a flat conveyor, comprising a center vacuum drum section, disposed to acquire and carry the center of each successive article to be transferred, a pair of outboard canted vacuum drums, each drum comprising a truncated cone section and disposed so as to acquire and carry an end of each successive product, wherein the angle of cant is such that at the point of most acute angle, the faces of the vacuum drums are approximately parallel to the ends of a presented article at its acquisition point and are parallel to and generally in plane with the face of the center vacuum drum section at the deposition point.

12. Apparatus according to claim 11 wherein said drum sections are not continuous, but rather are segments rotatable about central axes of said drum sections.

13. Apparatus according to claim 11 wherein the faces of the outboard drum sections are approximately but not exactly in the same plane as the center drum section at the point of deposition of said articles.

14. Apparatus according to claim 11 wherein the faces of each of the drum sections are provided with axially extending thickened portions across a portion of their circumferences whereby circumferential slippage of articles being transferred during rotation of said drum sections is minimized.

15. Apparatus according to claim 14 wherein thickened portions are formed by curved plates attached to the exterior drum section surfaces.

* * * * *